United States Patent
Rouse et al.

(10) Patent No.: US 11,364,186 B2
(45) Date of Patent: Jun. 21, 2022

(54) COMPOSITION, EMULSION, METHOD AND USE

(71) Applicant: Croda International Plc, Goole East Yorkshire (GB)

(72) Inventors: Sean Philip Nigel Rouse, East Yorkshire (GB); Emma Karen Mannion, West Yorkshire (GB); James Richard Humphrey, East Yorkshire (GB); Ben Cale, North Yorkshire (GB); Joshua Michael Moore, North Lincolnshire (GB)

(73) Assignee: Croda International PLC, Goole (GB)

( * ) Notice: Subject to any disclaimer, the term of this patent is extended or adjusted under 35 U.S.C. 154(b) by 129 days.

(21) Appl. No.: 16/069,609

(22) PCT Filed: Jan. 13, 2017

(86) PCT No.: PCT/EP2017/050661
§ 371 (c)(1),
(2) Date: Jul. 12, 2018

(87) PCT Pub. No.: WO2017/121847
PCT Pub. Date: Jul. 20, 2017

(65) Prior Publication Data
US 2020/0022892 A1    Jan. 23, 2020

(30) Foreign Application Priority Data
Jan. 15, 2016  (GB) ..................... 1600778

(51) Int. Cl.
| | | |
|---|---|---|
| *A61K 8/37* | (2006.01) | |
| *A61K 8/06* | (2006.01) | |
| *A61K 8/34* | (2006.01) | |
| *A61K 8/362* | (2006.01) | |
| *A61K 8/60* | (2006.01) | |
| *A61Q 15/00* | (2006.01) | |
| *A61Q 17/04* | (2006.01) | |
| *A61Q 19/00* | (2006.01) | |

(52) U.S. Cl.
CPC ............... *A61K 8/375* (2013.01); *A61K 8/06* (2013.01); *A61K 8/345* (2013.01); *A61K 8/362* (2013.01); *A61K 8/60* (2013.01); *A61Q 15/00* (2013.01); *A61Q 17/04* (2013.01); *A61Q 19/00* (2013.01); *A61K 2800/10* (2013.01); *A61K 2800/59* (2013.01)

(58) Field of Classification Search
CPC .................................................. A61K 8/375
See application file for complete search history.

(56) References Cited

U.S. PATENT DOCUMENTS

| | | | |
|---|---|---|---|
| 6,242,499 B1 | 6/2001 | Gruning et al. | |
| 7,851,511 B2 | 12/2010 | Allef et al. | |
| 8,334,400 B2 * | 12/2012 | Takeda | A61K 8/375 560/190 |
| 2002/0187170 A1 * | 12/2002 | Pavlin | A61Q 1/04 424/401 |
| 2007/0009465 A1 | 1/2007 | Lendlein et al. | |
| 2007/0190001 A1 * | 8/2007 | Jacques | A61Q 1/04 424/63 |
| 2010/0047194 A1 * | 2/2010 | Bevinakatti | C08G 63/21 424/59 |
| 2012/0110752 A1 * | 5/2012 | Lamberty | A61K 8/25 8/442 |

FOREIGN PATENT DOCUMENTS

| | | |
|---|---|---|
| DE | 102005029777 A1 | 1/2007 |
| EP | 0584692 A2 | 3/1994 |
| EP | 0623668 A2 | 11/1994 |
| EP | 0835862 A1 | 4/1998 |
| EP | 1500427 A2 | 1/2005 |
| WO | 9420067 A1 | 9/1994 |
| WO | 03063790 A2 | 8/2003 |
| WO | 2012007754 A1 | 1/2012 |
| WO | 2013174725 A2 | 11/2013 |

OTHER PUBLICATIONS

Breuer, T., "Dimer Acids", in J.I. Kroschwitz (ed.) Kirk-Othmer Encyclopedia of Chemical Technology, 4th Edition, 1993, vol. 8, pp. 223-237.
International Search Report and Written Opinion for International Application No. PCT/EP2017/050661, dated Jun. 27, 2017—8 pages.
English translation of Russian Search Report for Russian Application No. 2018129568, dated May 18, 2020, 2 pages.
Feng et al., "Synthesis and Kinetic Studies on Dimer Fatly Acid/ Polyethylene Glycol Polyester", Journal of Polymer Research, 2007, vol. 14, pp. 115-119.
Nikolaev, "Synthetic Polymers and Plastics Based on Them", Textbook for Chemical-Technol. Universitites and fac., 2nd Edition amended and before Leningrad: Chemistry, 1966, pp. 707-708.
Azarov et al., "Chemistry of Wood and Synthetic Polymers", Textbook for Universities, 1999, 7 pages.
Russian Ofifce Action for Russian Application No. 2018129568, dated Aug. 31, 2020, 5 pages.

* cited by examiner

*Primary Examiner* — Sarah Alawadi
(74) *Attorney, Agent, or Firm* — RatnerPrestia

(57) ABSTRACT

A composition which is the reaction product of reactants comprising dimer fatty acid and/or trimer fatty acid, a mono-alcohol comprising at least 3 carbon atoms and a polyol comprising at least 2 hydroxyl groups. The composition comprises dimer fatty diester and/or trimer fatty trimester, and oligoester comprising more than one dimer fatty acid and/or trimer fatty acid residue. The invention also provides an emulsion comprising the composition, particularly in the form of a personal care product, a method of emulsifying using the composition and use of the composition as an emulsifier.

13 Claims, No Drawings

COMPOSITION, EMULSION, METHOD AND USE

CROSS REFERENCE TO RELATED APPLICATIONS

This application is the National Stage filing of International Appln. No. PCT/EP2017/050661, filed Jan. 13, 2017, and claims priority of GB Application No. 1600778.3, filed Jan. 15, 2016, the entirety of which applications is incorporated herein by reference for all purposes.

FIELD OF INVENTION

The present invention relates to a composition, an emulsion comprising the composition, particularly in the form of a personal care product, a method of emulsifying using the composition and use of the composition as an emulsifier.

BACKGROUND

Alkoxylated esters have been used for many years as surface active agents (or surfactants), having emulsifying, dispersing, wetting and/or solubilising properties in a wide range of applications such as personal care, home care, industrial, food, and many others. In particular, alkoxylated esters have been used as emulsifiers in personal care applications, for example skin care, sunscreens, toiletries, decorative cosmetics, perfumes and fragrances.

Current commercially available alkoxylated esters are effective emulsifiers in many applications, but there is still a requirement to improve the properties of emulsifiers, particularly in personal care applications. These properties may include the flexibility of use of the emulsifier in different systems and the ability to emulsify in strenuous conditions such as a high internal phase content. An example of a further desirable property of an emulsifier would be if the emulsifier could be used in a particular system without the need for a co-emulsifier.

In addition, it may be desirable in some circumstances to use an emulsifier which has not been alkoxylated e.g. does not include any ethylene oxide or propylene oxide residues. A non-alkoxylated emulsifier may be desirable because the majority of alkylene oxides which are used in alkoxylation are derived from petrochemical feedstocks.

SUMMARY OF THE INVENTION

It is an object of the present invention to address at least one of the above or other disadvantages associated with the prior art.

Thus viewed from a first aspect, the present invention provides a composition which is the reaction product of reactants comprising:
 a) dimer fatty acid and/or trimer fatty acid;
 b) a mono-alcohol comprising at least 3 carbon atoms; and
 c) a polyol comprising at least 2 hydroxyl groups;
wherein the composition comprises:
 i) dimer fatty diester and/or trimer fatty triester; and
 ii) oligoester comprising more than one dimer fatty acid and/or trimer fatty acid residue.

Viewed from a second aspect, the present invention provides an emulsion comprising a composition of the first aspect.

Viewed from a third aspect, the present invention provides a personal care formulation comprising a composition according to the first aspect or an emulsion according to the second aspect.

Viewed from a fourth aspect, the present invention provides a method of stabilising an emulsion comprising the step of mixing a composition of the first aspect with the emulsion.

Viewed from a fifth aspect, the present invention provides the use of a composition of the first aspect to stabilise an emulsion.

All of the features described herein may be combined with any of the above aspects, in any combination.

The present invention is based in part on the recognition by the inventors that a composition of the first aspect of the invention has advantageous properties due to its particular combination of reactants. The mono alcohol and dimer/trimer fatty acid will react to form large hydrophobic domains. Without being bound by theory, the effects of steric hindrance will prevent the polyol from being fully esterified by these large hydrophobic domains. Therefore the polyol will maintain some residual hydroxyl functionality which will provide hydrophilicity. In this way more of the polyol's hydrophilic properties are maintained. These hydrophilic properties may reduce or remove the need for the composition to be alkoxylated. The combination of the large hydrophobic domains and the residual hydroxyl functionality on the polyol provides the composition with advantageous properties, for example as an emulsifier.

DETAILED DESCRIPTION OF THE INVENTION

It will be understood that any upper or lower quantity or range limit used herein may be independently combined.

It will be understood that, when describing the number of carbon atoms in a substituent group (e.g. 'C1 to C6'), the number refers to the total number of carbon atoms present in the substituent group, including any present in any branched groups. Additionally, when describing the number of carbon atoms in, for example fatty acids, this refers to the total number of carbon atoms including the one at the carboxylic acid, and any present in any branch groups.

Many of the chemicals which may be used to produce the composition of the present invention are obtained from natural sources. Such chemicals typically include a mixture of chemical species due to their natural origin. Due to the presence of such mixtures, various parameters defined herein can be an average value and may be non-integral.

The term 'residue' as used herein is the part of a reactant molecule which remains in the reaction product compound after a reaction has occurred.

Dimer & Trimer Fatty Acids

The terms 'timer fatty acid' and 'dimer fatty acid' are well known in the art, and refer to the trimerisation/dimerisation products of mono- or polyunsaturated fatty acids and/or esters thereof. They are described T. E. Breuer, 'Dimer Acids', in J. I. Kroschwitz (ed.), Kirk-Othmer Encyclopedia of Chemical Technology, 4th Ed., Wiley, New York, 1993, Vol. 8, pp. 223-237. They are prepared by polymerizing fatty acids under pressure, and then removing most of the unreacted fatty acid starting materials by distillation. The final product usually contains some mono fatty acid, mostly dimer fatty acids and trimer fatty acids, and some higher oligomeric fatty acids. The resultant product can be prepared with various levels of the different fatty acids. The ratio of dimer fatty acids to trimer fatty acids can be varied, by modifying the processing conditions and/or the unsaturated acid feedstock. The trimer fatty acid may be isolated in substantially pure form from the product mixture, using purification techniques known in the art, or alternatively a mixture of trimer fatty acid and dimer fatty acid may be used.

Preferred trimer fatty acids are trimers of $C_{10}$ to $C_{30}$, more preferably $C_{12}$ to $C_{24}$, particularly $C_{14}$ to $C_{22}$, and especially $C_{18}$ fatty acids. Thus, preferred trimer fatty acids contain in the range from 30 to 90, more preferably 36 to 72, particularly 42 to 66, and especially 54 carbon atoms. The molecular weight (weight average) of the trimer fatty acid is preferably in the range from 750 to 950, more preferably 790 to 910, particularly 810 to 890, and especially 830 to 870.

Suitable trimer fatty acids are the trimerisation products of oleic acid, linoleic acid, linolenic acid, palmitoleic acid, erucic acid and elaidic acid, and particularly of oleic acid. The trimer fatty acids may also be derived from the trimerisation products of the unsaturated fatty acid mixtures obtained in the hydrolysis of natural fats and oils, e.g. of sunflower oil, soybean oil, olive oil, rapeseed oil, cottonseed oil and tall oil.

The trimer fatty acids used herein preferably have an iodine value, measured as described herein, in the range from 30 to 150, more preferably 40 to 110, particularly 50 to 90, and especially 60 to 75 (measured as grams of iodine per 100 g of sample).

Non-hydrogenated or hydrogenated, for example by using a nickel catalyst, dimer and/or trimer fatty acids may be used. Hydrogenated dimer and/or trimer fatty acids are preferred, more preferably partially hydrogenated, yet more preferably fully hydrogenated.

Similarly, the dimer fatty acids are preferably derived from the dimerisation products of the materials mentioned in the above paragraph, and are preferably dimers of $C_{10}$ to $C_{30}$, more preferably $C_{12}$ to $C_{24}$, particularly $C_{14}$ to $C_{22}$, and especially $C_{18}$ fatty acids. Thus, the dimer fatty acids preferably contain in the range from 20 to 60, more preferably 24 to 48, particularly 28 to 44, and especially 36 carbon atoms. The molecular weight (weight average) of the dimer fatty acid is preferably in the range from 450 to 690, more preferably 500 to 640, particularly 530 to 610, and especially 550 to 590.

In one embodiment, substantially pure trimer fatty acids are esterified. In another embodiment, a composition comprising a mixture of trimer fatty acids and dimer fatty acids are esterified. The ratio of trimer fatty acids to dimer fatty acids is preferably in the range from 1% to 99%:1% to 99%, more preferably 5% to 95%:5% to 95%, yet more preferably 10% to 90%:10% to 90%, and particularly 15% to 85%:15% to 85% by weight.

Preferably, reactant a) comprises at least 50 wt % trimer fatty acid, particularly at least 65 wt %, desirably at least 70 wt %, especially at least 75 wt %, possibly at least 80 wt %. Preferably, reactant a) comprises less than 50 wt % dimer fatty acid, particularly less than 35 wt %, desirably less than 30 wt %, especially less than 25 wt %, possibly less than 20 wt %. Preferably, reactant a) comprises 70 to 90 wt % trimer fatty acid and 10 to 30 wt % dimer fatty acid.

When a dimer fatty acid molecule is fully esterified (i.e. all its acid groups are esterified), the product will be referred to as a 'dimer fatty diester'. When a trimer fatty acid molecule is fully esterified, the product will be referred to as a 'trimer fatty triester'.

The molecular weight (weight average) of the dimer fatty diester, measured by GPC as described herein, may be in the range from 500 to 1,500, preferably 600 to 1,400, more preferably 700 to 1,300, particularly 800 to 1,200 g/mol.

The molecular weight (weight average) of the trimer fatty triester, measured by GPC as described herein, may be in the range from 800 to 1,900, preferably 1,200 to 1,700, more preferably 1,300 to 1,600, particularly 1,350 to 1,550, and especially 1,400 to 1,500 g/mol.

The trimer fatty triester/dimer fatty diester may be produced by transesterification of a lower alkyl ester, preferably a $C_1$ to $C_6$ alkyl ester, more preferably a $C_1$ to $C_4$ alkyl ester, and particularly a $C_1$ to $C_2$ alkyl ester of trimer/dimer fatty acid.

In one preferred embodiment, the trimer fatty triester/dimer fatty diester is/are produced by direct esterification of trimer/dimer fatty acid.

Mono-Alcohol

The mono-alcohol reactant used in the present invention comprises at least 3 carbon atoms, preferably at least 6, desirably at least 8, especially at least 10. The mono-alcohol may comprise at most 24 carbon atoms, preferably at most 20, more preferably at most 16. Preferably, the mono-alcohol comprises from 6 to 18 carbon atoms.

The mono-alcohol is suitably a C6 to C18, preferably a C8 to C18, more preferably a C10 to C16, particularly C12 to C14, and especially a C12 mono-alcohol.

The mono-alcohol is preferably a primary mono-alcohol. The mono-alcohol may be linear or branched, saturated or unsaturated. The mono-alcohol is preferably a linear, more preferably saturated alcohol. The mono-alcohol may be a fatty alcohol.

Suitable linear mono-alcohols may be selected from the group consisting of propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, heneicosanol, docosanol, tricosanol and tetracosanol. Preferred mono-alcohols are decanol, undecanol, dodecanol, tridecanol, tetradecanol, pentadecanol and hexadecanol; more preferably decanol, undecanol, dodecanol, tridecanol and tetradecanol; and especially dodecanol.

In another embodiment, the mono-alcohol may be a branched, preferably saturated alcohol. Suitable branched mono-alcohols include isopalmityl alcohol and/or isostearyl alcohol. The branched mono-alcohol may also be a Guerbet alcohol, i.e. an alcohol formed by the Guerbet reaction. The Guerbet reaction is an organic reaction converting a primary aliphatic alcohol into its β-alkylated dimer alcohol with the loss of one equivalent of water. Preferred Guerbet alcohols include hexyl decyl alcohol, octyl decyl alcohol and octyl dodecyl alcohol.

There are various Guerbet alcohols on the market, e.g. Eutanol G/G16 (C16-C20 Guerbets) from BASF Personal Care and Nutrition GmbH. Sasol has various Isofol grades on the market (e.g. Isofol C12 to C32). Exxon has various Exxal C16 to C26 grades on the market, and Jarchem Industries supplies e.g. the Jarcol C12 to C36 grades. Evonik Goldschmidt GmbH supplies e.g. Tegosoft G 20.

Polyol

The term "polyol" is well known in the art, and refers to an alcohol comprising more than one hydroxyl group. The polyol reactant used in the present invention is preferably obtained from natural sources.

The polyol may comprise at least 3 hydroxyl groups, preferably at least 4. The polyol may comprise at most 12 hydroxyl groups, preferably at most 8, more preferably at most 6.

The polyol preferably comprises at least 3 carbon atoms. The polyol is suitably a C3 to C30 polyol, preferably a C3 to C15 polyol, more preferably a C4 to C12 polyol, particularly a C5 to C10, and especially a C6 to C9 polyol.

The polyol may be selected from a sugar, a sugar alcohol, glycerol, polyglycerol and mixtures thereof, preferably glycerol, polyglycerol and mixtures thereof, more preferably polyglycerol.

The term 'polyglycerol' as used herein means diglycerol, triglycerol, tetraglycerol, pentaglycerol, hexaglycerol, heptaglycerol, octaglycerol, nonaglycerol and decaglycerol and/or mixtures thereof. The polyglycerol component is preferably selected from the group consisting of diglycerol, triglycerol, tetraglycerol, pentaglycerol, and mixtures thereof; more preferably is selected from the group consisting of diglycerol, triglycerol, tetraglycerol and mixtures thereof; and particularly is selected from the group consisting of diglycerol, triglycerol and mixtures thereof. It is to be understood that commercially available polyglycerol is normally a mixture of polyglycerols and the term, e.g. "diglycerol" as used herein means that the main component is diglycerol and/or the average component, both by weight of the mixture is diglycerol. Equivalent meanings apply for the terms "triglycerol", "tetraglycerol" etc.

The polyglycerol used herein suitably comprises on average in the range from 2 to 10, preferably 2.2 to 7, more preferably 2.4 to 5, particularly 2.6 to 4, and especially 2.8 to 3.2 glycerol residues.

The glycerol and/or polyglycerol may be unsubstituted, i.e. the glycerol and polyglycerol may not have any substituents for or in any of their hydroxyl groups. In a preferred embodiment, the polyol reactant comprises at least 85 wt %, more preferably at least 90 wt %, and particularly at least 95 wt % of glycerol and/or polyglycerol. In one embodiment, the reaction to form the composition according to the present invention is carried out substantially in the absence of any polyols other than glycerol and/or polyglycerol.

In another embodiment, the polyol is a sugar, suitably comprising in the range from 4 to 25, more preferably 6 to 12 carbon atoms.

The sugar may be a monosaccharide, disaccharide, tetrasaccharide and/or oligo- or polysaccharide. Suitable monosaccharides include glucose, fructose and galactose. Suitable disaccharides include sucrose, maltose, lactose, cellobiose, trehalose and lactulose. The sugar preferably comprises, consists essentially of, or consists of a monosaccharide and/or disaccharide, more preferably a disaccharide, and particularly sucrose.

In a further embodiment, the polyol is a sugar alcohol, suitably of the molecular formula $C_aH_{2a+2}O_a$, wherein the value "a" is preferably in the range from 4 to 24, more preferably 5 to 12, and particularly 6. Suitable sugar alcohols include erythritol (4-carbon), threitol (4-carbon), arabitol (5-carbon), xylitol (5-carbon), ribitol (5-carbon), mannitol (6-carbon), sorbitol (6-carbon), galactitol (6-carbon), fucitol (6-carbon), and/or iditol (6-carbon).

The sugar alcohol may be selected from the group consisting of erythritol, threitol, arabitol, xylitol, ribitol, mannitol, sorbitol, galactitol, fucitol and iditol; more preferably sorbitol and mannitol, and particularly sorbitol.

The use of a mono-alcohol and a polyol in the composition will mean that some of the acid groups on the dimer/trimer acid will esterify with the mono-alcohol and some will esterify with the polyol. The ratios of reactants and extent of reaction may control the percentage of hydroxyl groups on the polyol which are esterified in the composition. If the polyol maintains some residual hydroxyl functionality (ie. OH groups which are not esterified) when reacted in the composition, this will provide hydrophilicity to the composition and may improve the properties of the composition as an emulsifier.

At least 10% of the hydroxyl groups which are present in the polyol reactant may be esterified in the composition, preferably at least 15%, more preferably at least 20%. At most 80% of the hydroxyl groups which are present in the polyol reactant may be esterified in the composition, preferably at most 60%, desirably at most 50%, particularly at most 40%. Preferably, 10 to 50% of the hydroxyl groups which are present in the polyol reactant are esterified in the composition.

It may be advantageous for the composition to comprise no or substantially no mono-carboxylic acid (mono-acid) as a reactant. A mono-acid may react with residual hydroxyl groups on the polyol and undesirably remove hydroxyl functionality from the composition. Preferably the composition includes less than 20 wt % mono-acid as a reactant, desirably less than 10 wt %, particularly less than 5 wt %. The composition may not comprise a linear mono-carboxylic acid as a reactant. The composition may not comprise hydroxystearic acid or polyhydroxystearic acid as a reactant.

Ratios of Reactants

The reactants for the composition comprise:
a) dimer fatty acid and/or trimer fatty acid;
b) a mono-alcohol comprising at least 3 carbon atoms; and
c) a polyol comprising at least 2 hydroxyl groups.

The ratios of reactants and extent of reaction may advantageously influence the properties of the composition.

Preferably, the molar amount of reactant b) in the composition is equal to or greater than the molar amount of reactant a). This may control the reaction of dimer/trimer acid a) with polyol c) and reduces the likelihood that oligoester is formed.

Preferably the molar amount of b) in the composition is equal to or greater than the molar amount of c). This may control the percentage of hydroxyl groups on the polyol which are esterified in the composition.

The composition comprises:
i) dimer fatty diester and/or trimer fatty triester; and
ii) oligoester comprising more than one dimer fatty acid and/or trimer fatty acid residue.

The average number of moles of mono-alcohol residue in the trimer fatty triester is suitably in the range from 0.2 to 2.9:1, preferably 1.0 to 2.7:1, more preferably 1.4 to 2.5:1, particularly 1.7 to 2.3:1, and especially 1.9 to 2.1:1.

The average number of moles of polyol residue in the trimer fatty triester is suitably in the range from 0.1 to 2.8:1, preferably 0.3 to 2:1, more preferably 0.5 to 1.6:1, particularly 0.7 to 1.3:1, and especially 0.9 to 1.1:1.

The average number of moles of mono-alcohol residue in the dimer fatty diester is suitably in the range from 0.1 to 1.9:1, preferably 0.4 to 1.6:1, more preferably 0.6 to 1.4:1, particularly 0.8 to 1.2:1, and especially 0.9 to 1.1:1.

The average number of moles of polyol residue in the dimer fatty diester is suitably in the range from 0.1 to 1.9:1, preferably 0.4 to 1.6:1, more preferably 0.6 to 1.4:1, particularly 0.8 to 1.2:1, and especially 0.9 to 1.1:1.

The trimer fatty triester is obtainable by reacting trimer fatty acid with mono-alcohol and polyol suitably at a molar ratio of 1:0.2 to 2.9:0.1 to 2.8, preferably 1:1.0 to 2.7:0.3 to 2, more preferably 1:1.4 to 2.5:0.5 to 1.6, particularly 1:1.7 to 2.3:0.7 to 1.3, and especially 1:1.9 to 2.1:0.9 to 1.1.

The dimer fatty diester is obtainable by reacting dimer fatty acid with mono-alcohol and polyol suitably at a molar ratio of 1:0.1 to 1.9:0.1 to 1.9, preferably 1:0.3 to 1.7:0.3 to 1.7, more preferably 1:0.5 to 1.5:0.5 to 1.5, particularly 1:0.7 to 1.3:0.7 to 1.3, and especially 1:0.9 to 1.1:0.9 to 1.1.

Reaction Method

The composition of the invention may be produced in a conventional esterification reaction, for example by reacting dimer and/or trimer fatty acid or lower alkyl ester thereof with mono-alcohol and polyol. The reaction may occur in one stage, i.e. where all of the reactants are mixed together and reacted, or in two stages, e.g. where the dimer/trimer fatty acid or lower alkyl ester thereof is mixed with the mono-alcohol and reacted together, followed by subsequent addition and reaction of the polyol. Preferably the reaction occurs in one stage.

The dimer fatty diester and/or trimer fatty triester is suitably obtainable by direct esterification of dimer and/or trimer fatty acid, acid chloride or acid anhydride with mono-alcohol and polyol; or by transesterification of a dimer and/or trimer fatty acid lower alkyl ester with mono-alcohol and polyol. If a dimer/trimer fatty acid lower alkyl ester is used, it is preferably a $C_1$ to $C_6$ alkyl ester, more preferably a $C_1$ to $C_4$ alkyl ester, and particularly a $C_1$ to $C_2$ alkyl ester. Preferably the dimer fatty diester and/or trimer fatty triester is obtainable by direct esterification of dimer and/or trimer fatty acid with mono-alcohol, preferably C6 to C24 fatty alcohol, and polyol.

Oligoester in Composition

The synthesis of the composition of the invention results in the production of materials comprising more than one dimer fatty acid residue and/or trimer fatty acid residue (these materials are referred to herein as 'oligoester'). Oligoester comprising:
  (i) 2 or 3 dimer and/or trimer fatty acid reaction residues in total is referred to herein as 'lower oligomeric ester';
  (ii) 4 or more dimer and/or trimer fatty acid reaction residues in total is referred to herein as 'higher oligomeric ester'.

The molecular weight (weight average) of oligoester, lower oligomeric ester and higher oligomeric ester may be measured by GPC as described herein.

The molecular weight of the oligoester is suitably in the range of 1,000 to 60,000, preferably 5,000 to 40,000, more preferably 6,000 to 30,000, particularly 8,000 to 20,000, and especially 10,000 to 14,000 g/mol.

The molecular weight of the lower oligomeric ester is suitably in the range from 1,000 to 5,000, preferably 2,500 to 4,500, more preferably 3,000 to 4,200, particularly 3,500 to 4,000, and especially 3,800 to 3,900 g/mol.

The molecular weight of the higher oligomeric ester is suitably in the range from 5,000 to 60,000, preferably 7,500 to 35,000, more preferably 10,000 to 30,000, particularly 12,500 to 25,000, and especially 14,000 to 18,000 g/mol.

The composition may comprise up to 100%, preferably in the range from 15 to 75%, more preferably 22 to 50%, particularly 25 to 40%, and especially 26 to 36% by weight of trimer fatty acid triester and/or dimer fatty acid diester, based on the total weight of the composition.

The composition may comprise in the range from 80 to 20%, preferably 75 to 45%, more preferably 70 to 60% and especially 70 to 65% by weight of oligoester, based on the total weight of the composition.

Preferably the composition comprises:
  i) 15 to 75% by weight of dimer fatty diester and/or trimer fatty acid triester; and
  ii) 80 to 20% by weight of oligoester;
based on the total weight of the composition.

In one embodiment, the composition may comprise (i) up to 100%, preferably in the range from 15 to 75%, more preferably 20 to 50%, particularly 25 to 35%, and especially 26 to 30% by weight of trimer fatty acid triester and/or dimer fatty acid diester; (ii) less than 50%, preferably in the range from 5 to 40%, more preferably 10 to 35%, particularly 15 to 30%, and especially 18 to 25% by weight of lower oligomeric ester; (iii) less than 75%, preferably in the range from 10 to 65%, more preferably 20 to 60%, particularly 35 to 55%, and especially 40 to 50% by weight of higher oligomeric ester, all based on total weight of the composition.

Unreacted Reactants

In one embodiment, the composition may also comprise unreacted mono-alcohol and/or polyol starting material. The concentration of unreacted mono-alcohol and/or polyol present in the composition is suitably less than 15%, preferably in the range from 0 to 10%, more preferably 0 to 7%, particularly 0 to 6%, and especially 0.1 to 5% by weight of the total composition.

The composition may comprise less than 20%, preferably less than 10%, more preferably less than 5%, particularly preferably less than 2%, and especially preferably no unreacted dimer and/or trimer fatty acid starting material, by weight of the total composition.

The Composition

The composition of the invention may be used to stabilise an emulsion. The composition may be an emulsifier.

The composition of the invention may have the properties of a surfactant, emulsifier, dispersant, stabiliser, solubiliser, pigment wetter and/or rheology modifier. The invention also includes the use of the composition as a surfactant, emulsifier, dispersant, stabilizer, solubiliser, pigment wetter and/or rheology modifier, preferably as a surfactant and/or emulsifier, more preferably as an emulsifier.

Preferably the composition does not comprise an alkylene oxide residue, more preferably the composition does not comprise a propylene oxide residue or an ethylene oxide residue, most preferably the composition does not comprise an ethylene oxide residue.

The composition may have an acid value (measured as described herein) in the range from 0 to 15, preferably 0 to 10, more preferably 0 to 5, particularly 0 to 2, and especially 0 to 1 mgKOH/g.

The composition may have a hydroxyl (OH) value (measured as described herein) in the range from 50 to 300, preferably 70 to 220, more preferably 80 to 190, particularly 90 to 175, and especially 90 to 165 mgKOH/g.

The composition may have a saponification (SAP) value (measured as described herein) in the range from 90 to 180, preferably 100 to 160, more preferably 110 to 150, particularly 115 to 140, and especially 120 to 130 mgKOH/g.

Use of the Composition in Emulsions

The composition of the invention is suitable for use in forming emulsions (and dispersions), i.e. as the, or as part of the, emulsifier system. The emulsion may be a water in oil emulsion, oil in polyol (e.g. glycerol) emulsion or oil in water emulsions. The emulsion may be a multiple emulsion, for example a water in oil in water emulsion.

The emulsion is preferably for use in a personal care formulation, more preferably a sunscreen, cosmetic, antiperspirant or dermatological product.

The composition of the invention is particularly suitable for the preparation of water-in-oil emulsions which provide water resistance and/or better moisturisation (for example, by occlusion).

The composition of the invention may be a high performance water in oil emulsifier. It may be used at a lower wt % inclusion level than an comparative emulsifier to provide an equivalent level of emulsion stability.

The oil phase of the emulsion preferably comprises an emollient oil of the type used in a personal care formulation. The emollient is preferably an oily material which is liquid at ambient temperature (i.e. about 23° C.). Alternatively it can be solid at ambient temperature, in which case in bulk it will usually be a waxy solid, provided it is liquid at an elevated temperature at which it can be included in and emulsified in the composition. The manufacture of the formulation preferably uses temperatures up to 100° C., more preferably about 80° C., and therefore such solid emollients will preferably have melting temperatures of less than 100° C., and more preferably less than 70° C. The emulsifier may be used cold process or using a semi-hot process if required.

The oil phase of the emulsion may comprise at least one ester oil, vegetable oil, alcohol, paraffin oil or silicone.

Suitable oil phase components include non-polar oils, for example mineral or paraffin, especially isoparaffin, oils, such as that sold by Croda as Arlamol (trade mark) HD; or medium polarity oils, for example vegetable ester oils such as jojoba oil, vegetable glyceride oils, animal glyceride oils, such as that sold by Croda as Crodamol (trade mark) GTCC (caprylic/capric triglyceride), synthetic oils, for example synthetic ester oils, such as isopropyl palmitate and those sold by Croda as Crodamol IPP and Arlamol DOA, ether oils, particularly of two fatty e.g. C8 to C18 alkyl residues, such as that sold by Cognis as Cetiol OE (dicaprylether), guerbet alcohols such as that sold by Cognis as Eutanol G (octyl dodecanol), or silicone oils, such as dimethicone oil such as those sold by Dow Corning as Xiameter PMX-200, cyclomethicone oil, or silicones having polyoxyalkylene side chains to improve their hydrophilicity; or highly polar oils including alkoxylate emollients for example fatty alcohol propoxylates such as that sold by Croda as Arlamol PS15E (propoxylated stearyl alcohol). Suitable emollient materials that can be solid at ambient temperature but liquid at temperatures typically used to make the formulations of this invention include jojoba wax, tallow and coconut wax/oil. When non-polar oils are used it may be desirable to use relatively high concentrations of the composition according to the present invention, in order to achieve suitably satisfactory emulsification, particularly to obtain small oil droplets.

Mixtures of emollients can and often will be used, and in some cases solid emollients may dissolve wholly or partly in liquid emollients or in combination the freezing point of the mixture is suitably low. Where the emollient composition is a solid (such as fatty alcohols) at ambient temperature, the resulting dispersion may technically not be an emulsion (although in most cases the precise phase of the oily disperse phase cannot readily be determined) but such dispersions behave as if they were true emulsions and the term emulsion is used herein to include such compositions.

The concentration of the oil phase may vary widely. The amount of oil in the emulsion is suitably in the range from 1 to 90%, preferably 3 to 60%, more preferably 5 to 40%, particularly 8 to 20%, and especially 10 to 15% by weight of the total formulation.

The amount of water (or polyol, e.g. glycerin) present in the emulsion is suitably greater than 5%, preferably in the range from 30 to 90%, more preferably 50 to 90%, particularly 70 to 85%, and especially 75 to 80% by weight of the total formulation.

The amount of composition of the invention in an emulsion or personal care formulation according to the present invention may be at least 0.1%, preferably at least 0.5%, more preferably at least 1%, particularly preferably at least 1.5%, and especially preferably at least 2%, by weight of the total formulation.

The amount of composition of the invention in an emulsion or personal care formulation according to the present invention may be at most 10%, preferably at most 8%, more preferably at most 7%, particularly preferably at most 6%, and especially preferably at most 5.5%, by weight of the total formulation.

The amount of composition of the invention in an emulsion or personal care formulation according to the present invention is suitably in the range from 0.1 to 10%, preferably 0.5 to 8%, more preferably 1 to 7%, particularly 1.5 to 6%, and especially 2 to 5.5%, by weight of the total formulation.

The emulsions according to the present invention may also contain other additional surfactant materials which form part of the emulsifier system. Other suitable surfactants include relatively hydrophilic surfactants, e.g. having a HLB value of greater than 10, preferably greater than 12, and relatively hydrophobic surfactants e.g. having a HLB value of less than 10, preferably less than 8. Relatively hydrophilic surfactants include alkoxylate surfactants with an average in the range from about 10 to about 100 alkylene oxide, particularly ethylene oxide residues; and relatively hydrophobic surfactants include alkoxylate surfactants preferably with an average in the range from about 3 to about 10 alkylene oxide, particularly ethylene oxide residues.

Personal care formulations according to the invention can be divided by viscosity into milks and lotions, which preferably have a low shear viscosity (measured at shear rates of about 0.1 to 10 $s^{-1}$ as is typically used in Brookfield viscometers) of up to 10,000 mPa·s, and creams which preferably have a low shear viscosity of more than 10,000 mPa·s. Milks and lotions preferably have a low shear viscosity in the range from 100 to 10,000, more preferably 200 to 5,000, and particularly 300 to 1,000 mPa·s. The amount of composition according to the present invention present in a milk or lotion is preferably in the range from 2 to 3% by weight of the total formulation.

Creams preferably have a low shear viscosity of at least 20,000, more preferably in the range from 30,000 to 80,000, and particularly 40,000 to 70,000 mPa·s, although even higher viscosities e.g. up to about $10^6$ mPa·s, may also be used. The amount of composition according to the present invention in a cream is preferably in the range from 2 to 3% by weight of the total formulation.

The emulsions of the invention may be made by generally conventional emulsification and mixing methods. For example, the composition of the invention may be added to (i) the oil phase, after which the aqueous phase is then added to the oil phase, or (ii) both the combined oil and water phases, or (iii) the water phase, which is then added to the oil phase. Method (i) is preferred. In all of these methods, the resulting mixture can then be emulsified using standard techniques. It is preferred to either heat the aqueous and oil phases usually above about 60° C., e.g. to about 80 to 85° C., or to subject the aqueous phase to high intensity mixing at lower, e.g. about ambient, temperature (cold process). Vigorous mixing and the use of moderately elevated temperatures can be combined if desired. The heating and/or high intensity mixing can be carried out before, during or after addition of the water to the oil phase.

The emulsions can also be made by inverse emulsification methods, whereby the composition of the invention is added to either the oil phase or the aqueous phase, and the aqueous phase is mixed into the oil phase to initially form a water in oil emulsion. Aqueous phase addition is continued until the system inverts to form an oil in water emulsion. Plainly a substantial amount of aqueous phase will generally be needed to effect inversion and so this method is not likely to be used for high oil phase content emulsions. Vigorous mixing and the use of moderately elevated temperatures can be combined if desired. Heating can be carried out during or after addition of the aqueous phase and before, during or after inversion. High intensity mixing can be carried out during or after addition of the aqueous phase, and before or during inversion The emulsions may for example be microemulsions or nanoemulsions, having a mean droplet size over a wide range, preferably in the range from 10 to 10,000 nm. In one embodiment, the emulsion droplet size may be reduced, for example by high pressure homogenisation, preferably to a value in the range from 100 to 1,000 nm, more preferably 300 to 600 nm.

The emulsions according to the present invention are stable, measured as described herein, preferably for greater than one month, more preferably greater than two months, particularly greater than three months, and especially greater than four months at ambient temperature, and also preferably at 40° C. The stability at even higher temperatures can be particularly important, and therefore the emulsion is stable, measured as described herein, suitably for greater than one week, preferably greater than two weeks, more preferably greater than 3 weeks, particularly greater than one month, and especially greater than two months at 50° C.

Personal Care Formulations

The composition of the invention is preferably for use in a personal care formulation, more preferably a sunscreen, cosmetic, colour cosmetic, deodorant, antiperspirant or dermatological product.

Many other components may be included in the formulation to make a personal care or cosmetic formulation or product. These components can be oil soluble, water soluble or non-soluble. Examples of such materials include:

(i) preservatives such as those based on potassium sorbate, sodium benzoate, parabens (alkyl esters of 4-hydroxybenzoic acid), phenoxyethanol, substituted ureas and hydantoin derivatives e.g. those sold commercially under the trade names Germaben II Nipaguard BPX and Nipaguard DMDMH. Such preservatives are used preferably at a concentration in the range from 0.5 to 2% by weight of the total composition. A preservative booster such as caprylyl glycol may also be used;

(ii) perfumes, when used preferably at a concentration in the range from 0.1 to 10% more preferably up to about 5%, and particularly up to about 2% by weight of the total composition;

(iii) humectants or solvents such as alcohols, polyols such as glycerol and polyethylene glycols, when used preferably at a concentration in the range from 1 to 10% by weight of the total composition;

(iv) sunfilter or sunscreen materials including organic sunscreens and/or inorganic sunscreens including those based on titanium dioxide or zinc oxide; when used preferably at a concentration in the range from 0.1% to 20%, more preferably 1 to 15%, and particularly 2 to 10% by weight of the total composition;

(v) alpha hydroxy acids such as glycolic, citric, lactic, malic, tartaric acids and their esters; self-tanning agents such as dihydroxyacetone;

(vi) antimicrobial, particularly anti-acne components such as salicylic acid;

(vii) vitamins and their precursors including: (a) Vitamin A, e.g. as retinyl palmitate and other tretinoin precursor molecules, (b) Vitamin B, e.g. as panthenol and its derivatives, (c) Vitamin C, e.g. as ascorbic acid and its derivatives, (d) Vitamin E, e.g. as tocopheryl acetate, (e) Vitamin F, e.g. as polyunsaturated fatty acid esters such as gamma-linolenic acid esters;

(viii) skin care agents such as ceramides either as natural materials or functional mimics of natural ceramides;

(ix) phospholipids, such as synthetic phospholipids or natural phospholipids, eg lecithin;

(x) vesicle-containing formulations;

(xi) germanium-containing compounds;

(xii) botanical extracts with beneficial skin care properties;

(xiii) skin whiteners such as Arlatone Dioic DCA (trade mark) sold by Croda, kojic acid, arbutin and similar materials;

(xiv) skin repair compounds actives such as Allantoin and similar series;

(xv) caffeine and similar compounds;

(xvi) cooling additives such as menthol or camphor;

(xvii) insect repellents such as N,N-diethyl-3-methylbenzamide (DEET) and citrus or eucalyptus oils;

(xviii) essential oils;

(xix) ethanol;

(xx) pigments, including microfine pigments, particularly oxides and silicates, e.g. iron oxide, particularly coated iron oxides, and/or titanium dioxide, and ceramic materials such as boron nitride;

(xxi) other solid components, such as are used in make up and cosmetics, to give suspoemulsions, preferably used in an amount in the range from 1 to 15 wt %, more preferably from 5 to 15 wt % based on the total weight of the formulation; and (xxii) deodorant or antiperspirant compounds.

The composition and emulsions according to the present invention are suitable for use in a wide range of formulations and end-use applications, such as moisturizers, sunscreens, after sun products, body butters, gel creams, high perfume containing products, perfume creams, baby care products, hair treatments, hair conditioners, skin toning and skin whitening products, water-free products, anti-perspirant and deodorant products, tanning products, cleansers, 2-in-1 foaming emulsions, multiple emulsions, preservative free products, mild formulations, scrub formulations e.g. containing solid beads, silicone in water formulations, pigment containing products, sprayable emulsions, cosmetics, colour cosmetics, conditioners, shower products, foaming emulsions, make-up remover, eye make-up remover, and wipes.

The formulation may be a spray, lotion, cream or ointment. When the formulation is a colour cosmetic, it may be a foundation, mascara, eyeshadow or lipstick. The formulation may be an anti-perspirant or deodorant.

Formulations containing a composition or emulsion according to the present invention may have a pH value over a wide range, preferably in the range from 3 to 13, more preferably 5 to 10, and especially 6 to 8.

Sunscreen

One preferred personal care formulation is a sunscreen which comprises one or more organic sunscreens and/or inorganic sunscreens such as metal oxides, but preferably comprises at least one particulate titanium dioxide and/or zinc oxide, particularly included in the composition in the form of an aqueous and/or organic, preferably aqueous, dispersion. Such titanium dioxide and/or zinc oxide dispersions are available commercially from Croda under the trade marks Tioveil, Solaveil and Spectraveil. In addition, organic sunscreens may be used together with the preferred metal oxide sunscreens, and include p-methoxy cinnamic acid esters, salicylic acid esters, p-amino benzoic acid esters, non-sulphonated benzophenone derivatives, derivatives of dibenzoyl methane and esters of 2-cyanoacrylic acid. Specific examples of useful organic sunscreens include benzophenone-1, benzophenone-2, benzophenone-3, benzophenone-6, benzophenone-8, benzophenone-12, isopropyl dibenzoyl methane, butyl methoxy dibenzoyl methane, ethyl dihydroxypropyl PABA, glyceryl PABA, octyl dimethyl PABA, octyl methoxycinnamate, homosalate, octyl salicylate, octyl triazone, octocrylene, etocrylene, menthyl anthranilate, 4-methylbenzylidene camphor, benzophenone 4, Methylene Bis-Benzotriazolyl Tetramethylbutylphenol, Bis-Ethylhexyloxyphenol Methoxyphenyl Triazine and phenyl benzimidazole sulphonic acid.

End use sunscreen formulations containing the surfactant composition according to the present invention can exhibit surprisingly improved water resistance and/or sun protection (SPF values).

Uses of the Composition Outside Personal Care

The composition or emulsion of the invention may also be used in products which are not personal care formulations.

A fuel may comprise the composition or emulsion of the invention. For example, the composition may be used in a fuel and water emulsion such as white diesel.

A lubricant may comprise the composition or emulsion of the invention. The lubricant may be an industrial, marine or automotive lubricant. The lubricant may be an emulsifiable lubricant. The lubricant may be a metalworking fluid.

A paint or coating may comprise the composition or emulsion of the invention. The composition may be used to emulsify water in an oil-based paint or coating formulation.

An agrochemical formulation may comprise the composition or emulsion of the invention.

The composition of the invention may be used to emulsify or disperse a hydrocarbon. The composition may be used as an asphaltene dispersant. The composition may be used as an emulsifier or stabiliser for an explosive. The explosive may be an emulsion explosive, for example an ammonium nitrate-fuel oil (ANFO) explosive.

The composition may be used as a pigment dispersant.

EXAMPLES

The invention is illustrated by the following non-limiting examples. All parts and percentages are given by weight unless otherwise stated.

It will be understood that all tests and physical properties listed have been determined at atmospheric pressure and ambient temperature (i.e. about 23° C.), unless otherwise stated herein, or unless otherwise stated in the referenced test methods and procedures.

Test Methods

In this specification the following test methods have been used:

(i) Emulsion stability was assessed by observing the emulsions after storage for 3 months at ambient temperature (23° C.), cold at 5° C. or under elevated temperature storage at 40° C., 45° C. and 50° C. Measuring storage stability at 50° C. is a severe test. The emulsions were also assessed for their freeze-thaw stability using a cycling oven (−10° C. to 40° C. in 24 hours). The composition was stable if no visible separation of the emulsion occurred. The stability of the emulsions was also assessed by monitoring the size of the dispersed phase water particles over a three month period. The particle size was measured using a Malvern Mastersizer 2000 that measures the size of the dispersed phase particles using laser diffraction.

(ii) Emulsion viscosity was measured at 23° C. with a Brookfield LVT viscometer using an appropriate spindle (LV1, LV2, LV3, or LV4) depending on the viscosity of the emulsion. The emulsion was tested at 6 rpm (0.1 Hz), 1 day after making the emulsion and results are quoted in mPa·s.

(iii) The hydroxyl value is defined as the number of mg of potassium hydroxide equivalent to the hydroxyl content of 1 g of sample, and was measured by acetylation followed by hydrolysation of excess acetic anhydride. The acetic acid formed was subsequently titrated with an ethanolic potassium hydroxide solution.

(iv) The acid value is defined as the number of mg of potassium hydroxide required to neutralise the free acids in 1 g of sample, and was measured by direct titration with a standard potassium hydroxide solution.

(v) The saponification (or SAP) value is defined as the number of mg of potassium hydroxide required for the complete saponification of 1 g of sample, and was measured by saponification with a standard potassium hydroxide solution, followed by titration with a standard sulphuric acid solution.

(vi) The iodine value is defined as the weight of iodine, $I_2$, in grams consumed by unsaturation in 100 g of sample, this is measured by reacting the sample with an excess of Wij's (Iodine monochloride) solution. The remaining Wij's solution is converted to Iodine with potassium iodide, the iodine is then titrated against a standard sodium thiosulphate solution.

(vii) Weight average molecular weight was determined by Gel Permeation Chromatography (GPC). The apparatus and settings used for the GPC are given in Table 1 below.

TABLE 1

| GPC apparatus and settings | |
|---|---|
| Spectrometer | Polymer labs GPC-50 |
| Detector | Refractive index |
| Columns | PL gel 31 μm 100 A & PL gel 5 μm mixed D |
| Solvent | Tetrahydrofuran (GPC grade). |
| Concentration of test substance | 1% |
| Colum temperature | 40° C. |
| Flow rate | 1 ml per minute |
| Injection Volume | 100 micro litre |
| Analysis time | 25 minutes |
| Method Type | Area Normalisation |
| Calibration | Relative, narrow standard calibration using PEG standards and a linear fit. The PEG standards had peak molecular weight (Mp) 106 to 3870 and were taken from an Aglient GPC/SEC Calibration kit, part number PL2070-0100 |

Example 1

1,540 g of trimer fatty acid (75 to 85% by weight of trimer fatty acid and 15 to 25% by weight of dimer fatty acid derived from oleic acid) and 2.2 g of palladium catalyst were charged into a 4 L, intrinsically safe pressure vessel (autoclave) with stirring, sample port, pressure relief valve, vent line and both nitrogen and hydrogen supply. The system was purged with nitrogen. The autoclave was pressure tested to ensure there were no leaks. The contents were heated to 200° C., with the stirrer off, the autoclave was purged with hydrogen and vented, before pressurising the vessel to 300 psi with hydrogen. The hydrogen flow meter was reset to 0 ml and the stirrer was started. Hydrogen pressure was maintained between 290-300 psi and the reaction continued for 2.5 hours. The stirrer was stopped and the hydrogen vented before being purged with nitrogen. The hydrogenated trimer acid product was cooled, discharged and then filtered to remove the catalyst. The product had Iodine Value=64.8 g $I_2$/100 g and Colour=7.7 Gardner.

207.54 g of the hydrogenated trimer acid, 81.91 g of dodecanol (>98 wt % purity), and 60.55 g of polyglycerol-3 were added to a 0.5 L flange flask. The flask was placed in a standard distillation set-up with overhead mixing (PTFE 40 mm centrifugal stirrer, 400 rpm) and a nitrogen sparge (about 20-30 cc/min). The mixture was heated to 175° C. for 4 hours, then 240° C. for 2.5 hours. The product was cooled and discharged. The product had Acid value=0.3 mgKOH/g, Saponification value=122.7 mgKOH/g, OH value=157.1 mgKOH/g.

Example 1A 1,575 g of trimer fatty acid (75 to 85% by weight of trimer fatty acid and 15 to 25% by weight of dimer fatty acid derived from oleic acid) and 2.26 g of palladium catalyst were charged into a 4 L, intrinsically safe pressure vessel (autoclave) with stirring, sample port, pressure relief valve, vent line and both nitrogen and hydrogen supply. The system was purged with nitrogen. The autoclave was pressure tested to ensure there were no leaks. The contents were heated to 230° C., with the stirrer off, the autoclave was purged with hydrogen and vented, before pressurising the vessel to 300 psi with hydrogen. The hydrogen flow meter was reset to 0 ml and the stirrer was started. Hydrogen pressure was maintained between 350-360 psi and the reaction continued for 1.5 hours. The stirrer was stopped and the hydrogen vented before being purged with nitrogen. The hydrogenated trimer acid product was cooled, discharged and then filtered to remove the catalyst. This product had Iodine Value=67.3 g $I_2$/100 g and Colour=7.4 Gardner.

200.70 g of the hydrogenated trimer acid, 100.30 g of dodecanol (>98 wt % purity), and 40.41 g of polyglycerol-3 were added to a 0.5 L flange flask. The flask was placed in a standard distillation set-up with overhead mixing (PTFE 40 mm centrifugal stirrer, 400 rpm) and a nitrogen sparge (about 20-30 cc/min). The mixture was heated to 175° C. for 4 hours, then 240° C. for 9 hours. The product was cooled and discharged. This product had Acid value=0.9 mgKOH/g, Saponification value=120.9 mgKOH/g, OH value=107.3 mgKOH/g.

Example 2

1,527 g of trimer fatty acid (75 to 85% by weight of trimer fatty acid and 15 to 25% by weight of dimer fatty acid derived from oleic acid) and 2.2 g of palladium catalyst were charged into a 4 L, intrinsically safe pressure vessel (autoclave) with stirring, sample port, pressure relief valve, vent line and both nitrogen and hydrogen supply. The system was purged with nitrogen and then vented. The autoclave was pressure tested to ensure there were no leaks. The contents were heated to 200° C., with the stirrer off, the autoclave was purged with hydrogen then vented, before pressurising the vessel to 300 psi with hydrogen. The hydrogen flow meter was reset to 0 ml and the stirrer was started. Hydrogen pressure was maintained between 290-300 psi and the reaction continued for 4.5 hours. The stirrer was stopped and the hydrogen vented before being purged with nitrogen. The hydrogenated trimer fatty acid product was cooled, discharged and then filtered to remove the catalyst. The product has Iodine Value=64.4 g $I_2$/100 g, Colour=6.8 Gardner.

203.97 g of the hydrogenated trimer acid), 80.51 g of dodecanol (>98 wt % purity) and 45.52 g of diglycerol were added to a 0.5 L flange flask. The flask was placed in a standard distillation set-up with overhead mixing (PTFE 40 mm centrifugal stirrer, 400 rpm) and a nitrogen sparge (about 20-30 cc/min). Then mixture was heated to 175° C. for 4 hours, then 240° C. for 2.5 hours. The product was cooled and discharged. The product had Acid value=0.5 mgKOH/g, Saponification value=128.5 mgKOH/g, OH value=145.2 mgKOH/g.

Example 3

A water-in-oil hydrating cream was made using a formulation listed in Table 2.

TABLE 2

| Hydrating Cream | | |
|---|---|---|
| Components | Ingredients | % w/w |
| Phase A | Arlamol ™ HD (Isohexadecane) (ex Croda) | 10.0 |
|  | Crodamol ™ DOA (Diethylhexyl adipate) (ex Croda) | 4.0 |
|  | Xiameter 245 (Cyclopentasiloxane) | 3.5 |
|  | White beeswax | 3.0 |
|  | Emulsifier produced in Example 1 or 2 | 2.0 |
|  | Arlamol ™ PS15E (PPG-15 stearyl ether) (ex Croda) | 1.5 |
|  | Aerosol R972 (Silica dimethyl silylate) | 0.5 |
| Phase B | Water | 25.1 |
|  | Sodium chloride | 4.0 |
|  | Sodium lactate (50% solution) | 7.4 |
|  | Renex ™ S30 (Sorbeth-30) (ex Croda) | 3.0 |
| Phase C | Urea | 12.0 |
|  | Water | 24.0 |

Procedure

The components of Phases A and B were combined separately and heated to 70° C. Phase B was then slowly added to Phase A with intensive stirring, homogenised for 1 minute (per 100 g), then stirred to 40° C. At 40° C., Phase C was added (urea dispersed in water) and the formulation was homogenised for 1 minute. The formulation was stirred to ambient temperature. Two formulations were made, the first using the Emulsifier of Example 1 and the second using the Emulsifier of Example 2.

The water-in-oil hydrating cream was subjected to the emulsion stability tests described above and was stable for at least 3 months at all temperatures and withstood 6 freeze-thaw cycles. The particle size of the dispersed phase water particles showed little change over the 3 month period demonstrating emulsion stability.

Example 4

A water-in-oil sunscreen was made using a formulation listed in Table 3.

TABLE 3

| Sunscreen | | |
|---|---|---|
| Components | Ingredients | % w/w |
| Phase A | Emulsifier produced in Example 1 or 2 | 3.0 |
| | Arlamol ™ HD (Isohexadecane) (ex Croda) | 12 |
| | Crodamol ™ DOA (Diethylhexyl adipate) (ex Croda) | 4.0 |
| | Crodamol ™ AB (C12-15 alkyl benzoate) (ex Croda) | 5.5 |
| | Solaveil ™ CT-100 (C12-15 alkyl benzoate (and) titanium dioxide (and) aluminium stearate (and) polyhydroxystearic acid (and) alumina) (ex Croda) | 12.0 |
| Phase B | Water | 58.8 |
| | Prisorine ™ 3515 (Isostearyl alcohol) (ex Croda) | 4.0 |
| | Magnesium sulphate heptahydrate | 0.7 |

Procedure

The components of Phases A and B were combined separately and heated to 70° C. Phase B was then slowly added to Phase A with intensive stirring, homogenised for 1 minute (per 100 g), and then stirred to ambient temperature. Two formulations were made, the first using the Emulsifier of Example 1 and the second using the Emulsifier of Example 2.

The water-in-oil sunscreen was subjected to the emulsion stability tests described above and was stable for at least 3 months at all temperatures and withstood 6 freeze-thaw cycles. The particle size of the dispersed phase water particles showed little change over the 3 month period demonstrating emulsion stability.

Example 5

A high internal phase light body cream was made using a formulation listed in Table 4.

TABLE 4

| Body cream | | |
|---|---|---|
| Components | Ingredients | % w/w |
| Phase A | Emulsifier produced in Example 1 or 2 | 1.0 |
| | Arlamol ™ PS15E (PPG-15 stearyl ether) (ex Croda) | 0.9 |
| | Xiameter 245 (Cyclopentasiloxane) | 2.1 |
| | Arlamol ™ HD (Isohexadecane) (ex Croda) | 6.0 |
| Phase B | Renex ™ S30 (Sorbeth-30) (ex Croda) | 4.5 |
| | Magnesium sulphate heptahydrate | 0.8 |
| | Water | 84.7 |

Procedure

The components of Phases A and B were combined separately and heated to 70° C. Phase B was then slowly added to Phase A with intensive stirring, homogenised for 1 minute (per 100 g), and then stirred to ambient temperature. Two formulations were made, the first using the Emulsifier of Example 1 and the second using the Emulsifier of Example 2.

The light body cream was subjected to the emulsion stability tests described above and was stable for at least 3 months at all temperatures and withstood 6 freeze-thaw cycles. The particle size of the dispersed phase water particles showed little change over the 3 month period demonstrating emulsion stability.

Example 6

Lower usage levels of the Emulsifier produced in Example 1 were investigated in the three formulations described in Examples 3 to 5. Formulations using 75% of the stated amount of the Emulsifier were tested for emulsion stability as described above. At these lower usage levels the formulations made with the Emulsifier produced in Example 1 remained stable over a 1 month test period.

Example 7

A water-in-oil antiperspirant cream was made using a formulation listed in Table 5.

TABLE 5

| Antiperspirant | | |
|---|---|---|
| Component | Ingredient | w/w % |
| Phase A | Emulsifier produced in Example 1 | 2.0 |
| | Arlamol ™ HD (Isohexadecane) (ex Croda) | 8.0 |
| | Cyclomethicone | 4.0 |
| | Arlamol ™ PS15E (PPG-15 stearyl ether) (ex Croda) | 3.0 |
| Phase B | Renex ™ S30 (Sorbeth-30) (ex Croda) | 10.0 |
| | Preservative | q.s. |
| | Water | 62.0 |
| Phase C | Aluminum chlorohydrate solution | 12.0 |

Procedure

The components of Phases A and B were combined separately and heated to 70° C. Phase B was then slowly added to Phase A with intensive stirring, homogenised for 1 minute (per 100 g), and then stirred to 50° C. Phase C was added slowly and the product formulation was stirred to ambient temperature.

Example 8

A water-free cream was made using a formulation listed in Table 6.

TABLE 6

| Water-free cream | | |
|---|---|---|
| Component | Ingredient | w/w % |
| Phase A | Emulsifier produced in Example 1 | 3.5 |
| | Arlamol ™ HD (Isohexadecane) (ex Croda) | 4.0 |
| | Crodamol ™ DOA (Diethylhexyl adipate) (ex Croda) | 1.5 |
| | Paraffin oil | 4.5 |
| | Crodamol ™ GTCC (Cappylic/capric triglyceride) (ex Croda) | 2.0 |
| | Aerosil R972 (Silica dimethyl silylate) | 0.5 |
| Phase B | Glycerol | 85.0 |
| | Preservative | q.s. |

Procedure

The components of Phases A and B were combined separately and heated to 75° C. Phase B was then slowly added to Phase A with intensive stirring, homogenised for 1 minute, and then stirred to ambient temperature.

Example 9

A cream foundation was made using a formulation listed in Table 7.

TABLE 7

Foundation

| Component | Ingredient | w/w % |
|---|---|---|
| Phase A | Emulsifier produced in Example 1 | 1.0 |
| | Crodamol ™ ISIS (Isostearyl isostearate) (ex Croda) | 5.0 |
| | DC246 Fluid (Cyclohexasiloxane, Cyclopentasiloxane) | 8.0 |
| | Cropure liquid vegelan | 1.0 |
| | Butyrospermum parkii (SHEA BUTTER) oil colour powder | 10.0 |
| | Tocopherol | 0.2 |
| | Propyl paraben | 0.1 |
| Phase B | Glycerin | 2.0 |
| | Methyl paraben | 0.2 |
| | Magnesium sulphate heptahydrate | 0.8 |
| | Disodium EDTA | 0.02 |
| | Water | To 100 |

Procedure

The components of Phases A and B were combined separately and heated to 85° C. Phase B was then slowly added to Phase A with intensive stirring, homogenised for 1 minute, and then stirred to ambient temperature.

Example 10

A water-in-oil-in-water multiple emulsion was made using a formulation listed in Table 8.

TABLE 8

Multiple emulsion

| Component | Ingredient | w/w % |
|---|---|---|
| Phase A | Arlamol ™ HD (Isohexadecane) (ex Croda) | 9.0 |
| | Crodamol ™ GTEH (Triethylhexanoin) (ex Croda) | 4.5 |
| | Arlamol ™ PS15E (PPG-15 stearyl ether) (ex Croda) | 4.5 |
| | Emulsifier produced in Example 1 | 2.4 |
| Phase B | Water | 33.2 |
| | Glycolic acid (57% aq) | 4.2 |
| | Ammonium hydroxide (25% aq) | 1.2 |
| | Magnesium sulphate heptahydrate | 0.4 |
| | Preservative | 0.6 |
| Phase C | Primary w/o emulsion from Phases A + B | 60 |
| Phase D | Water | 34.2 |
| | Glycerine | 3.0 |
| | Synperonic ™ PE/F127 Poloxamer 127 (ex Croda) | 2.0 |
| | Keltrol (Xanthan gum) | 0.7 |
| | Magnesium sulphate heptahydrate | 0.4 |
| | Preservative | q.s. |

Procedure

Phase B was adjusted to pH 3.5 with ammonium hydroxide. Phases A and B were heated separately to 70° C. Phase B was slowly added to Phase A with intensive stirring, homogenised for 1 minute, and cooled to room temperature with moderate stirring. Keltrol was pre-dispersed in water and the remaining Phase D ingredients added. Phase C was slowly added to Phase D with moderate stirring, homogenised for 1 minute, and cooled to room temperature with stirring.

Example 11

A leave in hair conditioner was made using a formulation listed in Table 9.

TABLE 9

Hair conditioner

| Components | Ingredients | % w/w |
|---|---|---|
| Phase A | Emulsifier produced in Example 1 | 1.0 |
| | Arlamol ™ HD (Isohexadecane) (ex Croda) | 1.0 |
| | Crodamol ™ STS (PPG-3 benzyl ether myristate) | 1.0 |
| | Xiameter 245 (Cyclopentasiloxane) | 2.0 |
| | Dow Corning 556 Cosmetic Grade Fluid (Phenyl trimethicone) | 3.0 |
| | Shea Butter | 1.0 |
| Phase B | Incroquat ™ CTC-30 (Cetrimonium chloride) (ex Croda) | 2.0 |
| | Croquat ™ WKP (Aqua (and) cocodimonium hydroxypropyl hydrolysed keratin) (ex Croda) | 0.5 |
| | Lactic acid | To pH 4.5 |
| | Sodium benzoate (and) potassium sorbate | 0.5 |
| | Water | 88.0 |

Procedure

The components of Phases A and B were combined separately and heated to 70° C. Phase B was then slowly added to Phase A with intensive stirring, homogenised for 1 minute (per 100 g), and then stirred to ambient temperature.

Example 12

A leave on hair moisturiser was made using a formulation listed in Table 10.

TABLE 10

Hair moisturiser

| Components | Ingredients | % w/w |
|---|---|---|
| Phase A | Emulsifier produced in Example 1 | 1.0 |
| | Arlamol ™ HD (Isohexadecane) (ex Croda) | 5.0 |
| | Borage Oil | 3.0 |
| | Magnesium stearate | 0.5 |
| | White beeswax (Cera alba) | 3.0 |
| | Grapeseed oil (Vitis vinifera) | 6.0 |
| | Pomegranate Seed Oil (Punica granatum) | 10.0 |
| Phase B | Water | 62 |
| | Renex ™ 30 (Sorbeth-30) (ex Croda) | 5.0 |
| | Urea | 4.0 |
| | Magnesium sulphate heptahydrate | 0.5 |
| | Preservative | q.s. |

Procedure

The components of Phases A and B were combined separately and heated to 70° C. Phase B was then slowly added to Phase A with intensive stirring, homogenised for 1 minute (per 100 g), and then stirred to ambient temperature.

Example 13

A water-in-oil sunscreen was made using a formulation listed in Table 11.

TABLE 11

Sunscreen

| Components | Ingredients | % w/w |
|---|---|---|
| Phase A | Emulsifier produced in Example 1 | 3.5 |
| | Arlamol ™ HD (Isohexadecane) (ex Croda) | 4.0 |
| | Arlamol ™ PS15E (PPG-15 stearyl ether) (ex Croda) | 9.0 |
| | Crodamol ™ AB (C12-15 alkyl benzoate) (ex Croda) | 5.0 |
| | Span ™ 83 (sorbitan Sesquioleate) (ex Croda) | 1.0 |
| | Solaveil ™ CT-200 (Titanium dioxide (and) isohexadecane (and) triethylhexanoin (and) aluminium stearate (and) alumina (and) polyhydroxystearic acid) (ex Croda) | 30.0 |
| | DC245 Fluid (Cyclopentasiloxane) | 2.0 |
| | Eusolex OCR (Octocrylene) | 4.0 |
| | Aerosil R972 (Silica dimethyl silylate) | 0.5 |
| | Bentone Gel TN (C12-15 alkyl benzoate (and) stearalkonium hectorite (and) propylene carbonate) | 3.0 |
| | Tinosorb S (Bis-ethylhexyloxyphenol methoxyphenyl triazine) | 2.0 |
| | Optisol ™ TD-50 (Titanium dioxide (and) caprylic/capric triglyceride (and) tri-PPG-3 myristyl ether citrate (and) sorbitan isostearate (and) polyglyceryl-3-polyricinoleate (and) manganese oxide) | 4.0 |
| Phase B | Pricerine 9091 (Glycerine) | 3.0 |
| | Tinosorb M (Methylene bis-benzotrizoyl tetramethylbutylphenol (and) aqua (and) decyl glucoside (and) propylene glycol (and xanthan gum) | |
| | Sodium chloride | 1.0 |
| | Preservative | q.s. |
| | Water | To 100 |

Procedure

The components of Phases A and B were combined separately and heated to 70° C. Phase B was then slowly added to Phase A with intensive stirring, homogenised for 1 minute (per 100 g), and then stirred to ambient temperature.

It is to be understood that the invention is not to be limited to the details of the above embodiments, which are described by way of example only. Many variations are possible.

The invention claimed is:

1. A composition which is the reaction product of reactants comprising:
    a) a dimer fatty acid and a trimer fatty acid;
    b) a mono-alcohol comprising at least 3 carbon atoms; and
    c) a polyol comprising at least 2 hydroxyl groups;
    wherein the composition comprises:
        i) 15 to 75 wt % based on the total weight of the composition of a combination of a dimer fatty diester and a trimer fatty triester further comprising at least one residue of the mono-alcohol, where the dimer fatty diester is present in an amount of less than 50 wt % of component i) and the trimer fatty triester is present in an amount of greater than 50 wt % of component i); and
        ii) an oligoester comprising more than one residue selected from a dimer fatty acid residue and a trimer fatty acid residue and further comprising at least one residue of the polyol.

2. The composition according to claim 1 wherein the molar amount of b) in the composition is equal to or greater than the molar amount of a).

3. The composition according to claim 1 wherein the molar amount of b) in the composition is equal to or greater than the molar amount of c).

4. The composition according to claim 1 which does not comprise an alkylene oxide residue.

5. The composition according to claim 1 wherein the polyol is selected from a sugar, a sugar alcohol, glycerol, polyglycerol and mixtures thereof.

6. The composition according to claim 1 wherein the mono-alcohol comprises from 6 to 18 carbon atoms.

7. The composition according to claim 1 having a hydroxyl value in the range from 90 to 300 mg KOH/g.

8. The composition according to claim 1 wherein 10 to 50% of the hydroxyl groups which are present in the polyol reactant are esterified in the composition.

9. The composition according to claim 1 wherein the composition comprises:
    80 to 20% by weight of the oligoester;
based on the total weight of the composition.

10. An emulsion comprising the composition according to claim 1.

11. A personal care formulation comprising the composition according to claim 1.

12. The personal care formulation according to claim 11 which is a sunscreen, cosmetic, colour cosmetic, deodorant, antiperspirant or dermatological product.

13. A method of stabilising an emulsion comprising the step of mixing the composition according to claim 1 with the emulsion.

* * * * *